United States Patent [19]
Narita et al.

[11] Patent Number: 6,040,165
[45] Date of Patent: Mar. 21, 2000

[54] MUTANT PRENYL DIPHOSPHATE SYNTHASE

[75] Inventors: Keishi Narita, Sendai; Chika Ishida, Aichi; Yoshie Takeuchi; Chikara Ohto, both of Toyota; Shinichi Ohnuma; Tokuzo Nishino, both of Sendai, all of Japan

[73] Assignee: Toyota Jidosha Kabushiki Kaisha, Toyota, Japan

[21] Appl. No.: 08/886,466

[22] Filed: Jul. 1, 1997

[30] Foreign Application Priority Data

Jul. 3, 1996 [JP] Japan .................................. 8-191635

[51] Int. Cl.[7] .............................. C12N 9/10; C12N 1/20; C12N 1/00; C07H 21/04
[52] U.S. Cl. ................... 435/193; 435/252.3; 435/320.1; 435/440; 435/832; 536/23.2
[58] Field of Search ................................ 435/193, 252.3, 435/320.1, 440, 832; 536/23.2

[56] References Cited

FOREIGN PATENT DOCUMENTS

| | | |
|---|---|---|
| 0 537 553 | 4/1993 | European Pat. Off. . |
| 0 674 000 A2 | 9/1995 | European Pat. Off. . |
| 0 733 709 | 9/1996 | European Pat. Off. . |

OTHER PUBLICATIONS

Ohnuma et al. (Aug. 2, 1996) vol. 271, pp. 18831–18837.
Math, et al., *Proc. Natl. Acad. Sci. USA*, vol. 89, Aug. 1992, pp. 6761–6764.
Ohnuma, et al., *J. Biol. Chem.*, 269:20, May 20, 1994, pp. 14792–14797.
Marrero et al., *J. Biol. Chem.*, 267:30, pp. 21873–21878, Oct. 25, 1992.
Koyama et al., *J. Biochem*, 113:3, pp. 355–363, 1993.
Koike–Takeshita et al., *J. Biol. Chem.*, 270:31, pp. 18396–18400, 1995.
Koyama et al., *Biochem.*, 33:42, pp. 12644–12648, 1994.
Koyama et al., *Biochem.*, 35:29, pp. 9533–9538, 1996.
Ohnuma et al., *J. Biol. Chem.*, 271:17, pp. 10087–10095, 1996.
Tarshis et al., *Biochem.*, 33:36, pp. 10871–10877, 1994.
Koyama et al., *Can. J. Chem.*, 72:75–79, 1994.

Primary Examiner—Rebecca E. Prouty
Assistant Examiner—Elizabeth Slobodyansky
Attorney, Agent, or Firm—Kenyon & Kenyon

[57] ABSTRACT

Manufacture or use of a mutant prenyl diphosphate synthase in which the amino acid residue located at the fifth position in the N-terminal direction from D of the N-terminal of the aspartic acid-rich domain DDXX(XX)D (the two X's in the parentheses may not be present) present in the second region among the conserved regions of the prenyl diphosphate synthase has been substituted by another amino acid.

6 Claims, 9 Drawing Sheets

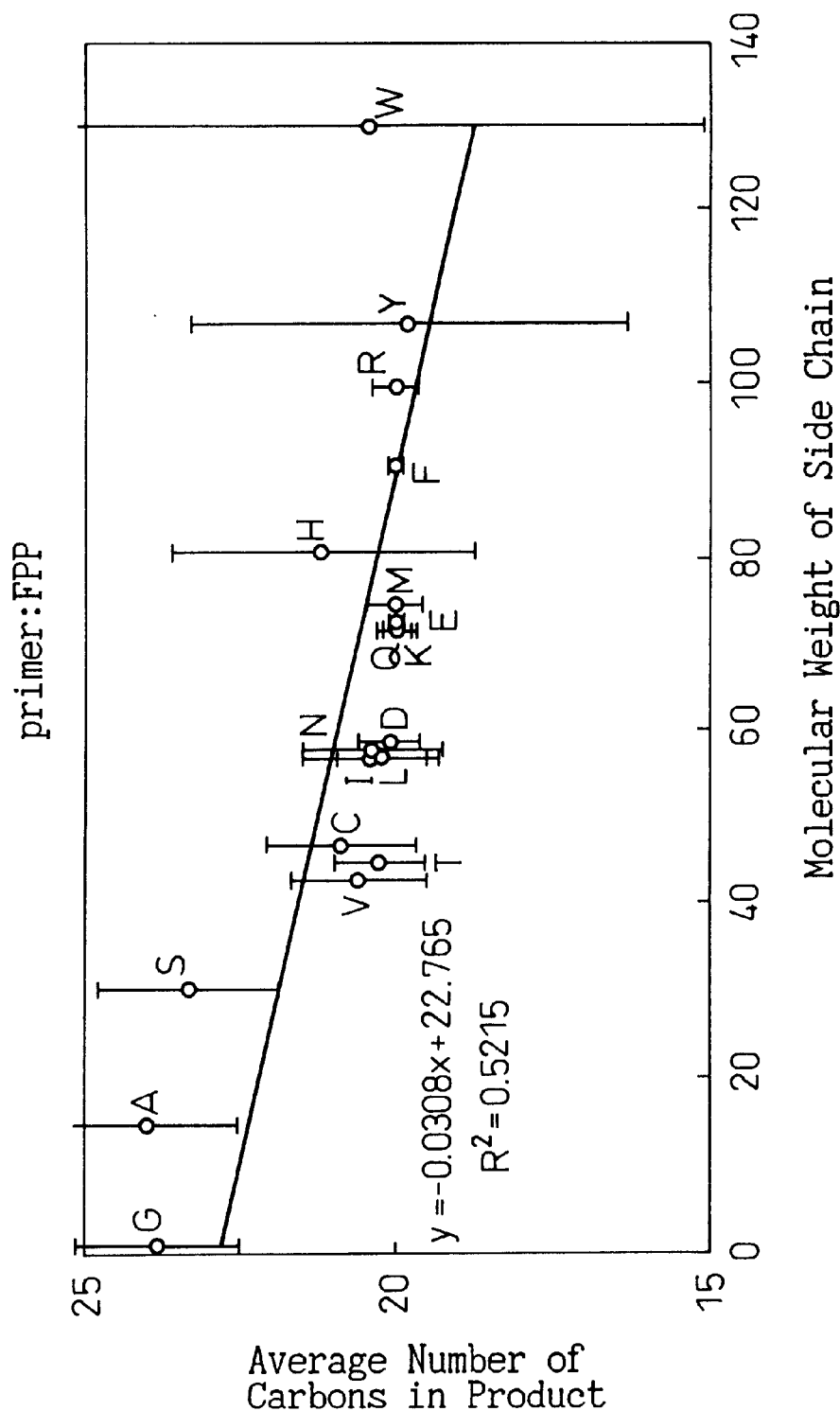

Fig. 11

Region I

```
       40 — Y S L E A G G K R I   R P L
1.     38 — Y G A L L G G K       R L
2.     46 — Y N T P G G K L       N R G L
3.     51 — Y N A I G G K Y       N R G L
4.     51 — Y N T V G G K Y       N R G L
5.
```

Region II

```
1.    73 — C A I   E M I H T Y S L I H D D L P S M D N D D L R R G K P T N
2.    75 — C   I           H A Y S L I H D D L P A M D D D D L R R G L P T C   C
3.    88 — C   I   E L L Q A Y F L V A D D M   M D K S I T R R G Q P   C
4.    91 — C       V E L L Q A F F L V A D D I       M D S S L T R R G Q   T C
5.    91 — C       V E L L Q A F F L V A D D I       M D S S H T R R G Q I   C
```

Region III

```
1.   115 — A   G D R       L L T Y A
2.   113 — A   G D A L Q T L       A
3.   125 — A I N D A F     M L   E A
4.   128 — A I N D A N     L L   E A
5.   128 — A I N D A       L L L E A
```

Region IV

```
1.   159 — G Q A A D M   K T G K M L Q Y S V H A G   A L I G   G   A D A R
2.   157 — G Q A L D L   K T G A   L I R A A V R L G A L S   A G   D K G
3.   167 — G Q L M D L   K T A Y Y S F Y L P V A L   A M Y V A G I T D E K
4.   170 — G Q T L D L   K T A F Y S F Y L P V A A   A M Y V A G I   D   K
5.   170 — G Q T L D L   K T A F Y S F Y L P V A A   A M Y V A G I   D   K
```

Region V

```
1.   285 — L   A Y I C E L V A A R D H
2.   287 — L E A   L A D Y I I Q R N K
3.   340 — L T A F L N   K V Y K R S K
4.   341 — L G   L A R K I Y K R S K
5.   342 — L E   L A N K I Y K R S K
```

Region VI

```
1.   217 — G L A F Q I R D D D I L D I E G A E E K I   G K P V G S D Q S N N K A T
2.   216 — G L A F Q V Q D D D I L D V V G D T A   T L G K R Q G A D Q Q L G K   S
3.   233 — G E Y F Q I Q D D Y L D C F G T P E Q I   G K I   G T D I Q D N K C S
4.   236 — G E F F Q I Q D D Y L D L F G D P S V T   G K I   G T D I Q D N K C S
5.   236 — G E F F Q I Q D D Y L D L F G D P S V T   G K V   G T D I Q D N K C S
```

Region VII

MUTANT PRENYL DIPHOSPHATE SYNTHASE

BACKGROUND OF INVENTION

1. Field of Invention

The present invention relates to novel mutant enzymes which synthesize linear prenyl diphosphates that are precursors of compounds, important to organisms, such as steroids, ubiquinones, dolichols, carotenoids, prenylated proteins, animal hormones, plant hormones, and the like, or a gene thereof etc.

2. Related Art

Of the substances having important functions in the body, many substances are biosynthesized using isoprene (2-methyl-1,3-butadiene) as a building block. These compounds are called isoprenoids, terpenoids, or terpenes, and are classified depending on the number of carbon atoms into hemiterpenes (C5), monoterpenes (C10), sesquiterpenes (C15), diterpenes (C20), sesterterpenes (C25), triterpenes (C30), tetraterpenes (C40), and the like. The actual synthesis starts with the mevalonate pathway through which mevalonic acid-5-diphosphate is synthesized, followed by the synthesis of isopentenyl diphosphate (IPP) which is an active isoprene unit.

The identity of the isoprene unit that was proposed as an speculated precursor was found to be IPP, the so-called active isoprene unit. Dimethylallyl diphosphate (DMAPP), an isomer of IPP, being used as a substrate in the reaction of isopentenyl adenine, which is known as a cytokinin and is one of the plant hormones, is also known to undergo condensation reaction with IPP to synthesize linear active isoprenoids such as geranyl diphosphate (GP), neryl diphosphate, farnesyl diphosphate (FPP), geranylgeranyl diphosphate (GGPP), geranylfarnesyl diphosphate (GFPP), hexaprenyl diphosphate (HexPP), heptaprenyl diphosphate (HepPP), and the like.

There are Z-type and E-type condensation reactions. GPP is a product of E-type condensation and neryl diphosphate is a product of Z-type condensation. Although, the all-E-type is considered to be the active form in FPP and GGPP, the Z-type condensation reactions lead to the synthesis of various polyprenols found in natural rubber, dolichols, bactoprenols (undecaprenols), and plants. They are believed to undergo the condensation reaction using the phosphate ester bond energy of the pyrophosphate and/or the carbon backbone present in the molecule to produce pyrophosphate and/or phosphate as the byproduct of the reaction.

FPP or GGPP serves as a reaction substrate leading to the synthesis of prenylated proteins (from FPP or GGPP) represented by G-proteins that are important in the mechanism of signal transduction in the cell; cell membrane lipids (from GGPP) of archaea; squalene (from FPP) which is a precursor of steroids; and phytoene (from GGPP) which is a precursor of carotenoid. Prenyl diphosphates from HexPP and HepPP having six and seven isoprene units respectively to prenyl diphosphates having ten isoprene units serve as the precursor of synthesis of ubiquinone and menaquinone (vitamin K2) that work in the electron transport system.

Furthermore, via the biosynthesis of these active-form isoprenoids, the following planty kinds of compounds that are vital to life have been synthesized. Just to mention a few, there are plant hormones of cytokinins and isopetenyl adenosine-modified tRNA that use hemiterpenes as their precursor for synthesis, monoterpene geraniol and the nerol isomers thereof that are the main components of rose oil perfume, and a camphor tree extract camphor which is an insecticide. Sesquiterpens include juvenile hormones of insects, diterpenes include a plant hormone gibberellin, trail pheromones of insects, and retinols and retinals that function as the visual pigment precursors, binding components of the purple membrane proteins of halophilic archaea, and vitamin A.

Furthermore, using squalene, a triterpene, a variety of steroid compounds have been synthesized, including, for example, animal sex hormones, vitamin D, ecdysone which is an mating hormone of insects, a plant hormone brassinolide, and components of plasma membranes. Various carotenoids of tetraterpenes that are precursors of various pigments of organisms and vitamin A are also important compounds derived from active isoprenoids. Compounds such as hlorophyll, pheophytin, tocopherol (vitamin E), and phylloquinone (vitamin K1) are also derived from tetraterpenes.

The active isoprenoid synthases that consecutively condense IPP with such allylic substrates DMAPP, GPP, FPP, GGPP, GFPP, and the like are called prenyl diphosphate synthases, and are also named, based on the maximum chain length of the major reaction products, for example farnesyl diphosphate synthase (FPP synthase), geranylgeranyl diphosphate (GGPP synthase), and the like. There are reports on purification, activity measurement, gene cloning, and its nucleotide sequencing of enzymes such as farnesyl diphosphate synthase, geranylgeranyl diphosphate synthase, hexaprenyl diphosphate synthase, heptaprenyl diphosphate synthase, octaprenyl diphosphate synthase, nonaprenyl diphosphate synthase (solanesyl diphosphate synthase), undecaprenyl diphosphate synthase, and the like from bacteria, archaea, fungi, plants, and animals.

These active isoprenoid synthases constituting the basis of synthesis of a great variety of compounds that are important both in the industry and in the field of life sciences have attracted little attention regarding their industrial applications due to their unstable character and low specific activities. However, with the isolation of the genes of FPP synthase and GGPP synthase from thermophilic bacteria and archaea [A. Chen and D. Poulter (1993) J. Biol. Chem. 268: 11002–11007, T. Koyama et al. (1993) J. Biochem. 113: 355–363, S. -i, Ohnuma et al. (1994) J. Biol. Chem. 269: 14792–14797], their availability as enzymes has increased.

The enzymes that synthesize prenyl diphosphates having 20 to 25 carbons are homodimers and are relatively easy to be reacted in vitro, as have been published in many reports. However, the enzymes that synthesize prenyl diphosphates having chain lengths exceeding the above-mentioned length are believed to be heterodimers, or to require additional factors such as a lipid, and the like. Therefore, in order to realize industrial application thereof, it was necessary to find optimal conditions that permit reassembly of two kinds of subunits or additional factors, which was a difficult task.

Therefore, there has been a need for the technology that enables to make the homodimer-type thermostable prenyl diphosphate synthases capable of synthesizing prenyl diphosphates having a longer chain length, by artificially altering the amino acid sequence of the homodimer type prenyl diphosphate synthases that are stable and have high specific activity derived from a thermophilic organism.

As for the prenyl diphosphate synthases derived from thermophilic organisms, there are at present examples of the altered FPP synthase derived from *Bacillus stearothermophilus* and GGPP synthase derived from *Sulfolobus acidocaldarius*. The mutant enzyme of FPP synthase of *Bacil-* lus stearothermophilus and the gene thereof were selected based on the color change of the organism by lycopene produced by coexistence of crtB (the gene of phytoene synthase) and crtI (the gene of phytoene desaturase, cis:trans isomerase) derived from Erwinia uredovora and the gene of FPP synthase of the mutant B. stearothermophilus in Escherichia coli. GGPP synthase and its mutant and the gene thereof of S acidocaldarius were selected based on the activity of complementing the glycerol metabolic activity of the HexPP synthase-deficient budding yeast of Saccharomyces cereviceae.

The coexistence method of the CrtB and CrtI genes of E. uredovora cannot be used for screening the reaction products longer than GGPP of the mutant enzyme, and the screening method using the complementation activity of the HexPP synthase-deficient budding yeast Saccharomyces cereviceae cannot be used for specific detection of the reaction products longer than HexPP. These genetic screening methods are capable of cloning the genes of the mutant prenyl diphosphate synthases having the synthetic activities of GGPP, GFPP, and HexPP, but cannot systematically control the chain length of the reaction products of prenyl diphosphate synthases with the intention of extending the chain length of the reaction products. A rule for that purpose is not known, either.

SUMMARY OF INVENTION

It is an object of the invention to establish a rule for systematic control of the chain length of reaction products by modifying amino acid residues of prenyl diphosphate enzymes. A new enzyme that is more stable or that has a high specific activity more adaptable to industrial application would make it possible to obtain immediately a mutant enzyme or the gene thereof that synthesizes prenyl diphosphate having a longer chain length by modifying amino acid residues based on the above rule.

From the information on the nucleotide sequence of the gene of GGPP synthase of the mutant S. acidocaldarius, it was clarified that out of the two proposed Asp-rich domains based on the analysis of the amino acid sequence of prenyl diphosphate synthase, the amino acid residue located at the fifth position upstream of the Asp-rich domain conserved sequence I (DDXX(XX)D) (SEQ ID NO. 9) at the amino terminal side is involved in the control of the chain length of reaction products.

Therefore, the present invention provides a mutant prenyl diphosphate synthase wherein an amino acid residue located at the fifth position in the N-terminal direction from D of the N-terminal of the Asp-rich domain DDXX(XX)D (SEQ ID NO. 9) (the two X's in the parentheses may not be present) present in the second region of the conserved regions of the original prenyl diphosphate synthase has been substituted by another amino acid.

The present invention also provides a DNA or a RNA encoding said enzyme.

The present invention further provides a recombinant vector comprising said DNA, specifically an expression vector.

The present invention further provides a host transformed by the above vector.

The present invention further provides a method for producing prenyl diphosphates having 20 carbons or more characterized in that the above enzyme is contacted with a substrate selected from the group consisting of isopentenyl diphosphate, dimethylallyl diphosphate, geranyl diphosphate, farnesyl diphosphate, and geranylgeranyl diphosphate.

The present invention further provides a method for producing the enzyme as set forth in any of claims 1 to 4, said method comprising culturing the above-mentioned host and then harvesting the expression product from the culture.

BRIEF EXPLANATION OF THE DRAWINGS

FIG. 10 is a graph showing the relationship between average chain length of the reaction products when FPP was used as the allylic substrate and the molecular weights of the amino acid side chains.

FIG. 11 is a graph showing the regions (I) to (VII) of various prenyl diphosphate synthases and Asp-rich domains, and the amino acid (asterisk) positioned at the fifth position in the N-terminal direction from the end thereof. In the figure, the sequence represents the amino acid sequence of farnesyl diphosphate synthase, 1 is the one derived from Bacillus stearothermophilus, 2 from Escherichia coli, 3 from Saccharomyces cereviceae, 4 from a rat, and 5 from a human.

DETAILED DESCRIPTION

Figure 1:
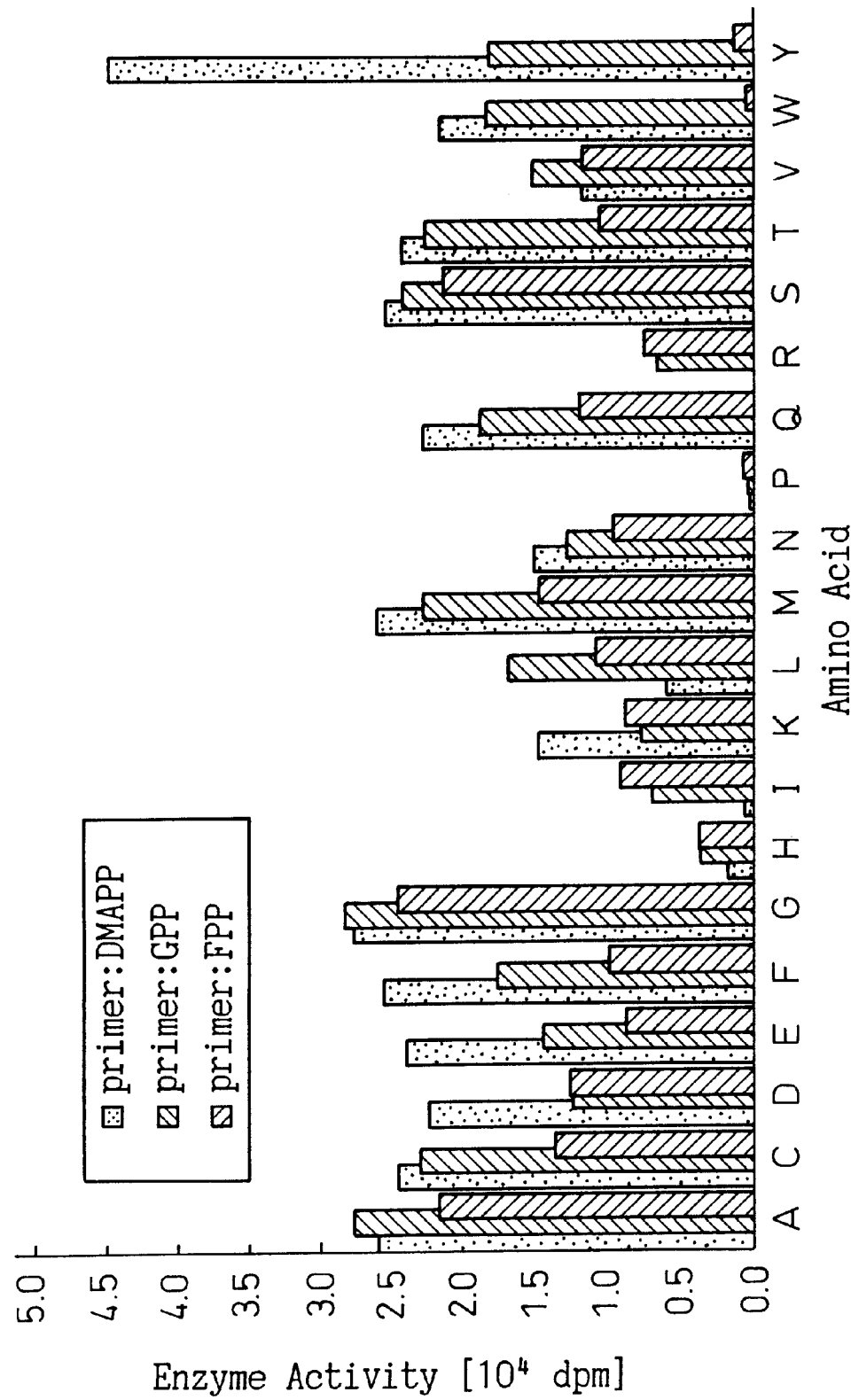
FIG. 1 is a graph showing the enzymatic activity of the 19 mutant type BstFPSs (B. stearothermophilus FPP synthase) obtained and a wild type BstFPS (sample name Y). "primer: DMAPP" indicates that DMAPP was used as the allylic substrate, "primer: GPP" indicates that GPP was used as the allylic substrate, and "primer: FPP" indicates that FPP was used as the allylic substrate. In the samples named A to W, the name of amino acid after introduction of substitution at position 81 is indicated by a one-letter code.

It has been proposed that there are seven conserved regions in the amino acid sequences of prenyl diphosphate synthase (one subunit in the case of a heterodimer) (A. Chem et al., Protine Science Vol. 3, pp. 600–607, 1994). It is also known that of the five conserved regions, the region II containing an Asp-rich domain conserved region I [DDXX(XX)D] (SEQ ID NO. 9) (the two X's in the parentheses may not be present). Although there is also an Asp-rich domain in region IV, the Asp-rich domain used to specify the modified region of the amino acid sequence of the present invention is present in region II, said domain being termed as the aspartic acid-rich domain I as compared to the aspartic acid-rich domain II present in region VI.

As to the prenyl diphosphate synthases having the Asp-rich domain as described above, there can be mentioned farnesyl diphosphate synthase, geranylgeranyl diphosphate synthase, hexaprenyl diphosphate synthase, heptaprenyl diphosphate synthase, octaprenyl diphosphate synthase, nonaprenyl diphosphate synthase, undecaprenyl diphosphate synthase, and the like. More specific examples include farnesyl diphosphate synthase of *Bacillus stearothermophilus*, farnesyl diphosphate synthase of *Escherichia coli*, farnesyl diphosphate synthase of *Saccharomyces cereviceae*, farnesyl diphosphate synthase of the rat, farnesyl diphosphate synthase of the human, geranylgeranyl diphosphate synthase of *Neurospora crassa*, hexprenyl diphosphate synthase of *Saccharomyces cereviceae*, and the like.

By way of example of some of these, regions I to VII and the Asp-rich domain I (in the box) in region II of the amino acid sequence of farnesyl diphosphate synthases are shown in FIG. 11.

The present invention can be applicable to the prenyl diphosphate synthases having these aspartic acid-rich domains I.

According to the present invention, the amino acid residue located at the fifth position in the N-terminal direction from the amino acid D of the N-terminal of the amino acid sequence constituting said Asp-rich domain I "DDXX(XX)D" (SEQ ID NO. 9) (the two X's in the parentheses may not be present) is substituted by another amino acid. This amino acid is indicated by an asterisk in FIG. 11. The amino acid after substitution may be any naturally occurring amino acid other than the original amino acid. As one such example there is mentioned an enzyme having the amino acid sequence in which amino acid tyrosine at the position 81 in SEQ ID No: 1 has been substituted by a naturally occurring amino acid.

Many mutant prenyl diphosphate syntheses of the present invention can synthesize a prenyl diphosphate having a longer chain length than that synthesized by the native prenyl diphosphate synthase. For example, some of the farnesyl diphosphate synthases that can synthesize a farnesyl diphosphate having 15 carbons, when modified into a mutant enzyme, can synthesize hexaprenyl diphosphate having 30 carbons.

It is known that an enzyme may retain its original enzymatic activity even when its original amino acid sequence is modified by addition, deletion, and/or substitution of one or a few amino acids. Therefore, the present invention is intended to encompass, in addition to the peptides having the amino acid sequence as set forth in SEQ ID No: 1, those enzymes that contain amino acid sequences modified by substitution, deletion, and/or addition of one or a few, for example up to 5, or up to 10, amino acids, and that can perform its original function.

The present invention also provides the genes encoding various above-mentioned mutant enzymes, the vectors containing those genes, specifically expression vectors, and the hosts transformed with said vectors. The gene (DNA) of the present invention can be readily obtained, for example, by introducing mutation into the DNA encoding the native amino acid sequence as set forth in SEQ ID No: 1 using site-specific mutagenesis or other conventional methods such as PCR and the like.

Furthermore, once the amino acid sequence of the desired enzyme has been determined, an appropriate nucleotide sequence thereof can be determined and the DNA can be chemically synthesized in accordance with a conventional method of DNA synthesis.

The present invention further provides an expression vector comprising DNA such as the one mentioned above, the host transformed with said expression vector, and a method for producing the enzyme or peptide of the present invention using these hosts.

Expression vectors contain an origin of replication, expression regulatory sequences etc., but they may differ with the hosts. As to the hosts, there can be mentioned procaryotes, for example, bacteria such as *Escherichia coli*, and genus Bacillus such as *Bacillus subtilis*, as well as eucaryotes, for example, fungi such as yeast, for example genus Saccharomyces, such as *Saccharomyces cereviceae*, genus Pichia such as *Pichia pastoris*, filamentous fungi, for example genus Aspergillus such as *Aspergillus oryzae* and *Aspergillus niger*, animal cells, for example the cultured cell of the silkworm, cultured cells of higher animals such as CHO cell, and the like. Furthermore, plants may be used as the host.

As shown in Examples, in accordance with the present invention during culturing the host transformed by the DNA of the present invention, long-chain prenyl diphosphates such as GGPP, GFPP, Hexpp, and the like may be accumulated in the culture medium, which may be recovered to produce their respective diphosphates. Furthermore, in accordance with the invention, long-chain prenyl diphosphates may also be produced by bringing the mutant prenyl diphosphate synthase produced in accordance with the invention in contact with a substrate isopentenyl diphosphate and allyl substrate such as farnesyl diphosphate.

When *Escherichia coli* is used as the host, it is known that the host has the regulatory functions of the gene at the stage of transcribing mRNA from DNA and of translating protein from mRNA. As the promoter sequence regulating mRNA synthesis, there are known, in addition to the naturally occurring sequences (for example, lac, trp, bla, lpp, $P_L$, $P_R$, ter, T3, T7, etc.), their mutants (for example, lacUV5), and the sequences (such as tac, trc, etc.) in which a naturally occurring promoter is artificially fused, and they can be used for the present invention.

It is known that the distance between the sequence of the ribosome biding site (GAGG and similar sequences thereof) and the initiation codon ATG is important as the sequence regulating the ability of synthesizing protein from mRNA. It is also well known that a terminator (for example, a vector containing rrnPT1 T2 commercially available from Pharmacia) that directs completion of transcription termination at the 3'-end affects the efficiency of protein synthesis by a recombinant.

As to the vectors that can be used for preparation of the recombinant vectors of the present invention, various vectors may be mentioned that are derived depending on the intended use. For example, there can be mentioned pBR322, pBR327, pKK223-3, pKK233-3, pTrc99, and the like having a replicon derived from pMB1; pUC18, pUC19, pUC118, pUC119, pTV118N, pTV119N, pBluescript, pHSG298, pHSG396, and the like that have been altered to enhance copy numbers; or pACYC177, pACYC184, and the like that have a replicon derived from p15A; and, furthermore, plasmids derived from pSC101, ColE1, R1, F factor, and the like. Furthermore, fusion protein-expressing vectors that enable easier purification such as pGEX-2T, pGEX-3X, pMal-c2 may be used. One example of the gene used as the starting material of the present invention is described in Japanese patent application No. 6-315572.

Furthermore, in addition to plasmids, virus vectors such as λ phage or M13 phage, or transposon may be used for introduction of genes. With regard to the introduction of the gene into microorganisms other than *Escherichia coli*, gene introduction into organisms of genus Bacillus by pHY300PLK (Takara Shuzo) is known. These vectors are described in Molecular Cloning (J. Sambrook, E. F. Fritsch, and T. Maniatis, Cold Spring Harbor Laboratory Press) and Cloning Vector (P. H. Pouwels, B. E. Enger, Valk, and W. J. Brammar, Elsevier), and catalogues of many manufacturers.

pTrc99is particularly preferable since it has, in addition to a selectable marker of the ampicillin resistant gene, a promoter, regulatory genes such as Ptrc and $lacI^q$, the sequence AGGA as the ribosome binding site, $rrnPT_1T_2$ as the terminator, and the function of regulating expression of the gene of FPP synthase.

Integration of the DNA fragment encoding the prenyl diphosphate synthase and, where needed, the DNA fragment having the function of regulating expression of the gene of said enzyme into these vectors can be performed by a known method using an appropriate restriction enzyme and ligase. Specific examples of the plasmids thus constructed include, for example, pTV118N-Bst FPS.

As the microorganisms used for integration of genes by such recombinant vectors, *Escherichia coli* and microorganisms of the genus Bacillus may be used. Such a transformation can also be carried out using the $CaCl_2$ method and the protoplast method as described in Molecular Cloning (J. Sambrook, E. F. Fritsch, and T. Maniatis, Cold Spring Harbor Laboratory Press) and DNA Cloning Vol. I to III (D. M. Clover ed., IRL PRESS).

In order to produce the mutant enzyme of the present invention, a host transformed as above is cultured, and then said culture is subjected to any method comprising salting out, precipitation with an organic solvent, gel chromatography, affinity chromatography, hydrophobic interaction chromatography, ion exchange chromatography, and the like to recover and purify said enzyme.

The present invention also provides a process for producing prenyl diphosphates using the enzyme of the present invention. According to this method, the enzyme of the present invention is reacted in a medium, particularly an aqueous medium, and then, as desired, the prenyl diphosphate is recovered from the reaction medium. As the enzyme, not only a purified enzyme but also a crude enzyme that may be semi-purified to various stages, or a mixture of the cultured biomass of a microorganism may be used. Alternatively there may be used immobilized enzymes prepared according to the conventional method from said enzyme, crude enzyme, or product containing the enzyme.

As the substrate, there may be used prenyl diphosphates and isopentenyl diphosphates having 5 to 20, preferably 5, carbons fewer than the number of carbons of the desired prenyl diphosphate. As the reaction medium, water or an aqueous buffer solution, for example Tris buffer or phosphate buffer and the like, may be used.

By using the system of regulating chain length of the reaction product of prenyl diphosphate synthase obtained by the present invention, the prenyl diphosphate having longer chain length, synthesis of which has so far been possible only with the hetero-dimer type enzyme, can be synthesized using mutant prenyl diphosphate synthase of the homo-dimer type that is easier to handle. Furthermore, by modifying the amino acid residue located five amino acids upstream of the aspartic acid-rich domain I of the corresponding subunit having the aspartic acid-rich domain of the hetero-dimer type prenyl diphosphate synthase using the above system, creation of the mutant enzyme that synthesizes prenyl diphosphates having further longer chains can be expected.

In the claims and the specification of the present invention, amino acid residues are expressed by the one-letter codes or three-letter codes:

A; Ala; alanine
C; Cys; cystine
D; Asp; aspartic acid
E; Glu; glutamic acid
F; Phe; phenylalanine
G; Gly; glycine
H; His; histidine
I; Ile; isoleucine
K; Lys; lysine
L; Leu; leucine
M; Met; methionine
N; Asn; asparagine
P; Prl; proline
Q; Gln; glutamine
R; Arg; arginine
S; Ser; serine
T; Thr; threonine
V; Val; valine
W; Trp; tryptophan
Y; Tyr; tyrosine Substitution of amino acid is expressed in the order of "the amino acid residue before substitution," "the number of the amino acid residue," and "the amino acid residue after substitution." For example, the mutation in which a tyrosine residue at position 81 is replaced with a methionine residue is expressed as Y81M.

EXAMPLES

The present invention is now explained with reference to specific examples, but they must not be construed to limit the invention in any way.

Example 1

Construction of a plasmid containing the gene of FPP synthase

The gene of FPP synthase (hereinafter referred to as BstFPS) derived from *Bacillus stearothermophilus* was subcloned at the NcoI-HindIII site of the plasmid vector pTV118N commercially available from Takara Shuzo. The plasmid DNA was designated as pTV118N-BstFPS. The BstFPS gene is available from *Escherichia coli* JM109 (pEX1) that was internationally deposited on Sep. 26, 1991 with the National Institute of Bioscience and Human-Technology, Agency of Industrial Science and Technology, of Ibalaki, Japan under the accession number of FERM BP-3581. Also, the entire nucleotide sequence of the BstFPS gene has been published in Japanese patent application 3(1991)-253788, T. Koyama et al., (1993) J. Biochem. 113:355–363, or in the genetic information data bank such as GenBank under the accession number D13293. Since *Bacillus stearothermophilus* is also available from various depositories of microorganisms such as ATCC etc., the DNA of the gene of BstFPS region can be obtained by the conventional gene cloning method.

Example 2

Synthesis of the oligonucleotides for introducing mutation

For introduction of mutation of the gene of FPP synthase, the following oligonucleotides were designed and synthesized:

```
Primer DNA (Y81X): 5'GAT CCA TAC GNN NTC TTT GAT TCA TGA TGA TTT G3' (SEQ ID No:2)

Primer DNA (Y81N): 5'GAT CCA TAC GAA CTC TTT GAT TCA TGA TGA TTT G3' (SEQ ID No:3)

Primer DNA (Y81I): 5'GAT CCA TAC GAT TTC TTT GAT TCA TGA TGA TTT G3' (SEQ ID No:4)

Primer DNA (Y81M): 5'GAT CCA TAC GAT GTC TTT GAT TCA TGA TGA TTT G3' (SEQ ID No:5)

Primer DNA (Y81F): 5'GAT CCA TAC GTT CTC TTT GAT TCA TGA TGA TTT G3' (SEQ ID No:6)

Primer DNA (Y81P): 5'GAT CCA TAC GCC GTC TTT GAT TCA TGA TGA TTT G3' (SEQ ID No:7)

Primer DNA (Y81V): 5'GAT CCA TAC GGT GTC TTT GAT TCA TGA TGA TTT G3' (SEQ ID No:8)
```

They are designed to newly introduce the cleavage site of the restriction enzyme BspHI (5'TCATGA3') as well as to introduce mutation in the codon encoding the amino acid residue at position 81 of BstFPS. The introduction of the cleavage site of BspHI does not change the amino acid sequence encoded by the BstFPS gene due to degeneracy of codons. This is used to detect the substitution-mutated plasmid by means of agarose gel electrophoresis after digestion with BspHI, since the introduction of mutation by substitution to the amino acid residue at position 81 of the BstFPS gene simultaneously produces a new BspHI cleavage site.

These primer DNA's were subjected to phosphorylation at 37° C. for 30 minutes in the reaction medium shown below followed by denaturation at 70° C. for 10 minutes:

| 10 pmol/µl primer DNA | 2 µl |
|---|---|
| 10 x kination buffer | 1 µl |
| 10 mM ATP | 1 µl |
| H₂O | 5 µl |
| T4 polynucleotide kinase | 1 µl | in which the 10 x kination buffer is 1000 mM Tris-Cl (pH 8.0), 100 mM MgCl₂, and 70 mM DTT.

Example 3

Introduction of substitution mutation into the codon corresponding to the amino acid residue at position 81 of the BstFPS gene Using each primer DNA constructed in Example 2, substitution mutation was introduced into the plasmid prepared in Example 1 in accordance with the Kunkel method. Mutan-K kit commercially available from Takara Shuzo was used to perform the Kunkel method. The experimental procedure was as described in the kit insert. The substitution mutation of the plasmid need not be conducted by the Kunkel method. For example, the same result can be obtained by a method using the polymerase chain reaction (PCR).

Using *Escherichia coli* CJ236 in the Mutan-K kit as the host cell, a single strand DNA was obtained in which the thymine base in plasmid pTV118N-BstFPS was replaced with deoxyuracil base.

The single stranded DNA thus obtained was used as the template in a reaction in which a primer DNA for synthesizing a complementary strand was treated in the following reaction solution at 65° C. for 15 minutes and then annealed by allowing to stand at 37° C. for 15 minutes:

| Single strand DNA | 0.6 pmol |
|---|---|
| Annealing buffer solution | 1 µl |
| Primer DNA solution (Example 2) | 1 µl |
| H₂O make to a final volume of 10 µl | | in which the annealing buffer solution is 200 mM Tris-Cl (pH 8.0), 100 mM MgCl₂, 500 mM NaCl and 10 mM DTT.

Furthermore, 25 µl of an extention buffer solution, 60 units of *Escherichia coli* DNA ligase, and 1 unit of T4 DNA polymerase were added to synthesize a complementary strand at 25° C. for 2 hours. The extention buffer solution is 50 mM Tris-Cl (pH 8.0), 60 mM ammonium acetate, 5 MM MgCl₂, 5 mM DTT, 1 mM NAD, and 0.5 mM dNTP.

After the reaction is over, 3 µl of 0.2M EDTA (pH 8.0) was added thereto and was subjected to treatment at 65° C. for 5 minutes to stop the reaction.

Example 4

Construction of a recombinant having a gene in which substitution mutation has been introduced into the codon corresponding to the amino acid residue at position 81 of the BstFPS gene In accordance with Example 3, the DNA solution constructed was used to transform *Escherichia coli* DH5α by the CaCl₂ method. An alternative method such as the electroporation gives the same result.

The transformant obtained by the CaCl₂ method was plated onto the agar plate containing ampicillin, a selectable marker of transformants, and was incubated overnight at 37° C.

Among the transformants obtained as above, those substitution-mutated pTV118N-BstFPS plasmid that has a BspHI cleavage site in BstFPS coding region was selected. The nucleotide sequence in the neighborhood of the codon corresponding to the amino acid residue at position 81 of the BstFPS gene of the selected substitution mutated pTV118N-

BstFPS plasmid was determined by the dideoxy method. As a result, the pTV118N-BstFPS plasmids containing the following 19 substitution mutated BstFPS genes were obtained:

| Mutation | Codon |
|---|---|
| Y81A | GCT |
| Y81C | TGC |
| Y81D | GAC |
| Y81E | GAA |
| Y81F | TTC |
| Y81G | GGT |
| Y81H | CAC |
| Y81I | ATT |
| Y81K | AAG |
| Y81L | CTC |
| Y81M | ATG |
| Y81N | AAC |
| Y81P | CCG |
| Y81Q | CAA |
| Y81R | AGG |
| Y81S | TCG |
| Y81T | ACA |
| Y81V | GTG |
| Y81W | TGG |
| Y81Y(wild type) | TAC |

Example 5

Measurement of activity of the mutant BstFPS

Crude enzyme solutions were prepared as follows from 20 transformants comprising 19 mutant BstFPS genes obtained in Example 4 and one wild type BstFPS gene.

The transformant cultured overnight in the 2 x LB medium was centrifuged to harvest cells, and then the cells were suspended into the buffer for cell homogenization (50 mM Tris-Cl (pH 8.0), 10 mM meracptoethanol, 1 mM EDTA). This was homogenized by sonication and then centrifuged at 4° C. at 10,000 r.p.m. for 10 minutes. The supernatant was treated at 55° C. for 30 minutes to inactivate the activity of prenyl diphosphate synthase derived from *Escherichia coli*. This was further centrifuged under the same condition and the supernatant obtained was used as a crude enzyme extract in the reaction of 55° C. for 15 minutes in the following reaction solution:

| | |
|---|---|
| [1-$^{14}$C]-IPP (1 Ci/mol) | 25 nmol |
| Allylic substrate (DMAPP or GPP or FPP) | 25 nmol |
| Tris-Cl (pH 8.5) | 50 mM |
| MgCl$_2$ | 5 mM |
| NH$_4$Cl | 50 mM |
| β-mercaptoethanol | 50 mM |
| Enzyme solution | 50 μg |
| H$_2$O to make 1 ml | |

After the reaction is over, 3 ml of butanol is added to extract the reaction product into a butanol layer. One ml of the butanol layer obtained was added into 3 ml of liquid scintiilator to measure radioactivity by a scintillation counter. The result is shown in FIG. 1. Y81P mutant BstFPS has exhibited very little enzymatic activity, which is inferably due to the fact that only the proline amino residue is derived from the imino acid, and therefore it is unable to take the form of α-helix or β-sheet structure, thereby significantly changing the essential higher structure itself of the enzyme.

Figure 2:
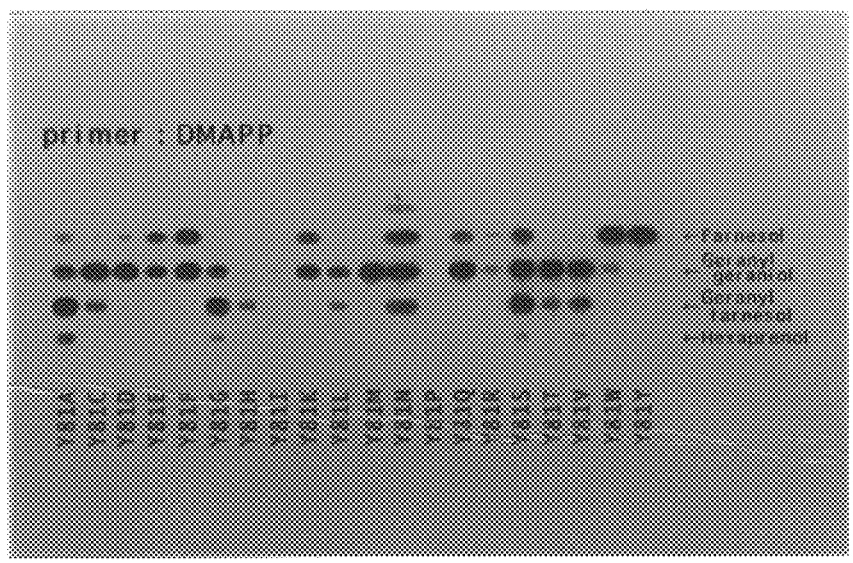
FIG. 2 shows a photograph of a development pattern of TLC of the dephosphorylated product of the mutant BstFPSs' reaction when DMAPP was used as the allylic substrate. Y81A to Y81Y represent amino acid substitution mutations.
Figure 3:
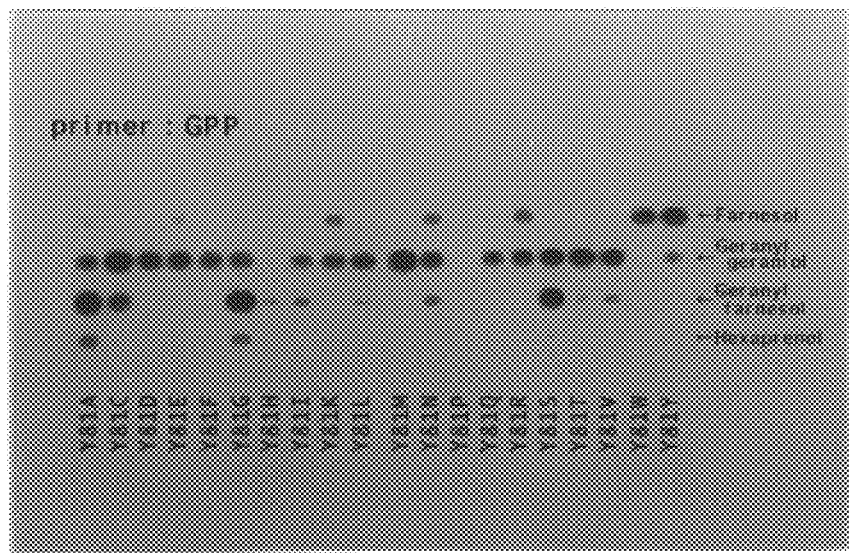
FIG. 3 shows a photograph of a development pattern of TLC of the dephosphorylated product of the mutant BstFPSs' reaction when GPP was used as the allylic substrate. Y81A to Y81Y represent amino acid substitution mutations.

The solvent is evaporated from remainder of the butanol layer by purging nitrogen gas thereinto while heating the layer to concentrate to 0.5 ml. To the concentrate were added two ml of ethanol and one ml of potato acid phosphatase solution (2 mg/ml potato acid phosphatase, 0.5M sodium acetate (pH 4.7)) to effect the dephosphorylation reaction at 37° C. Subsequently dephosphorylated reaction product was extracted with 3 ml of n-pentane. This was concentrated by evaporating the solvent by purging nitrogen gas thereinto, which was then analyzed by TLC (reverse phase TLC plate: LKC18 (Whatman), development solvent: acetone/water=9/1). The developed dephosphorylated reaction product was analyzed by the Bio Image Analyzer BAS2000 (Fuji Photo Film) to determine the location and the relative radioactivity. When the amount ratio of all the reaction products is identical, the ratio of radioactivity becomes FPP:GGPP:GFPP:HexPP=2:3:4:5. The result when DMAPP was used as the allylic substrate is shown in FIG. 2, when GPP was used as the allylic substrate in FIG. 3, and when FPP was used as the allylic substrate in FIG. 4.

Example 6

Figure 4:
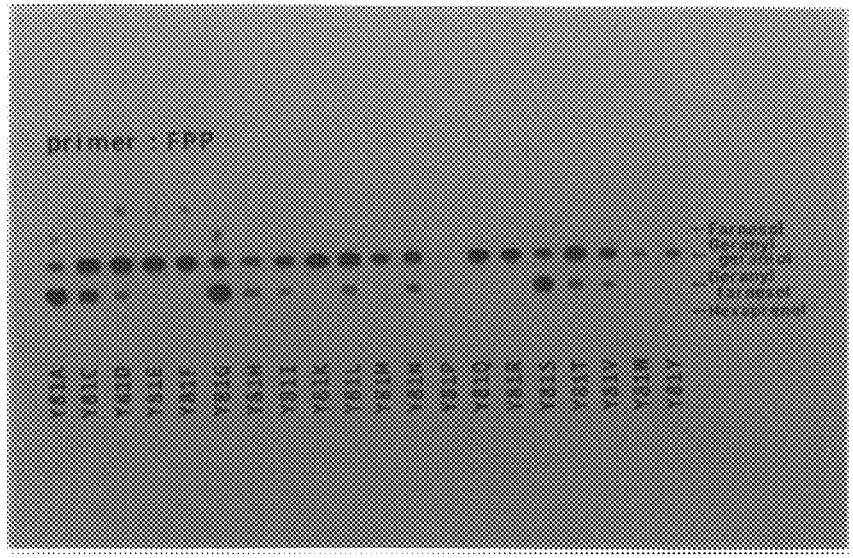
FIG. 4 shows a photograph of a development pattern of TLC of the dephosphorylated product of the mutant BstFPSs' reaction when EPP was used as the allylic substrate. Y81A to Y81Y represent amino acid substitution mutations.

Relation of the substitution-mutated amino acid residue and chain length of the reaction product FIG. 1 and FIG. 4 show that when the reaction was carried out using FPP as the allylic substrate most of the mutant BstFPSs converts IPP to prenyl diphosphates having chain length longer than GGPP. At this time, the substitution mutants in which the side chains of the amino acids are such small molecules as glycine, alanine, and serine have a higher activity, whereas the substitution mutants in which the side chains of the amino acids are such large wild type molecules as tyrosine and tryptophan show a lower activity.

Then, the enzymatic activity were plotted against the molecular weights of the side chains (FIG. 5, FIG. 6, and FIG. 7) with regard to the amino acid residue at position 81. However, the Y81P substitution mutant enzyme in which enzymatic function was lost is excluded.

Figure 7:
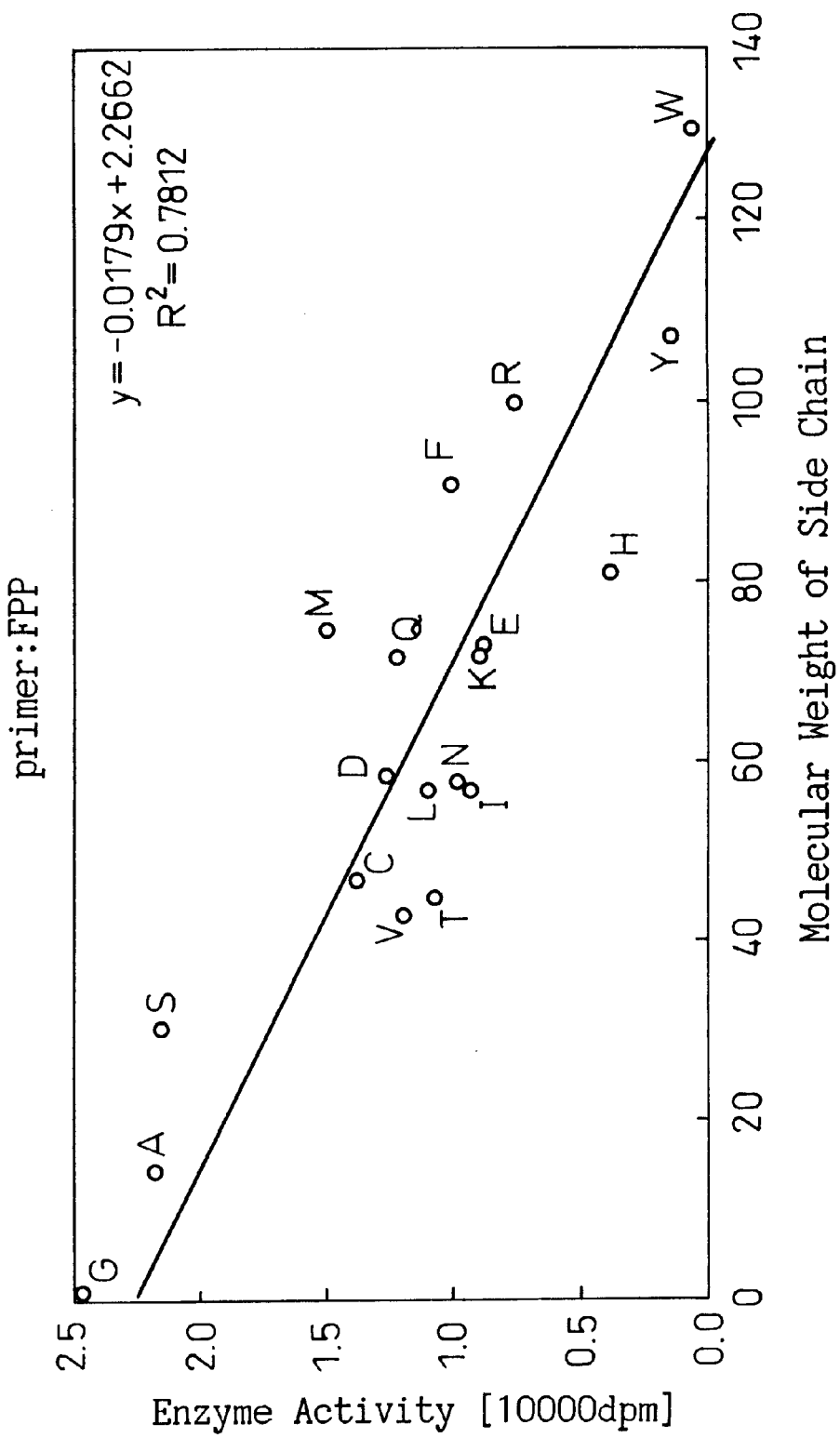
FIG. 7 is a graph showing the relationship between the enzymatic activity when FPP was used as the allylic substrate and the molecular weights of the amino acid side chains.
Figure 8:
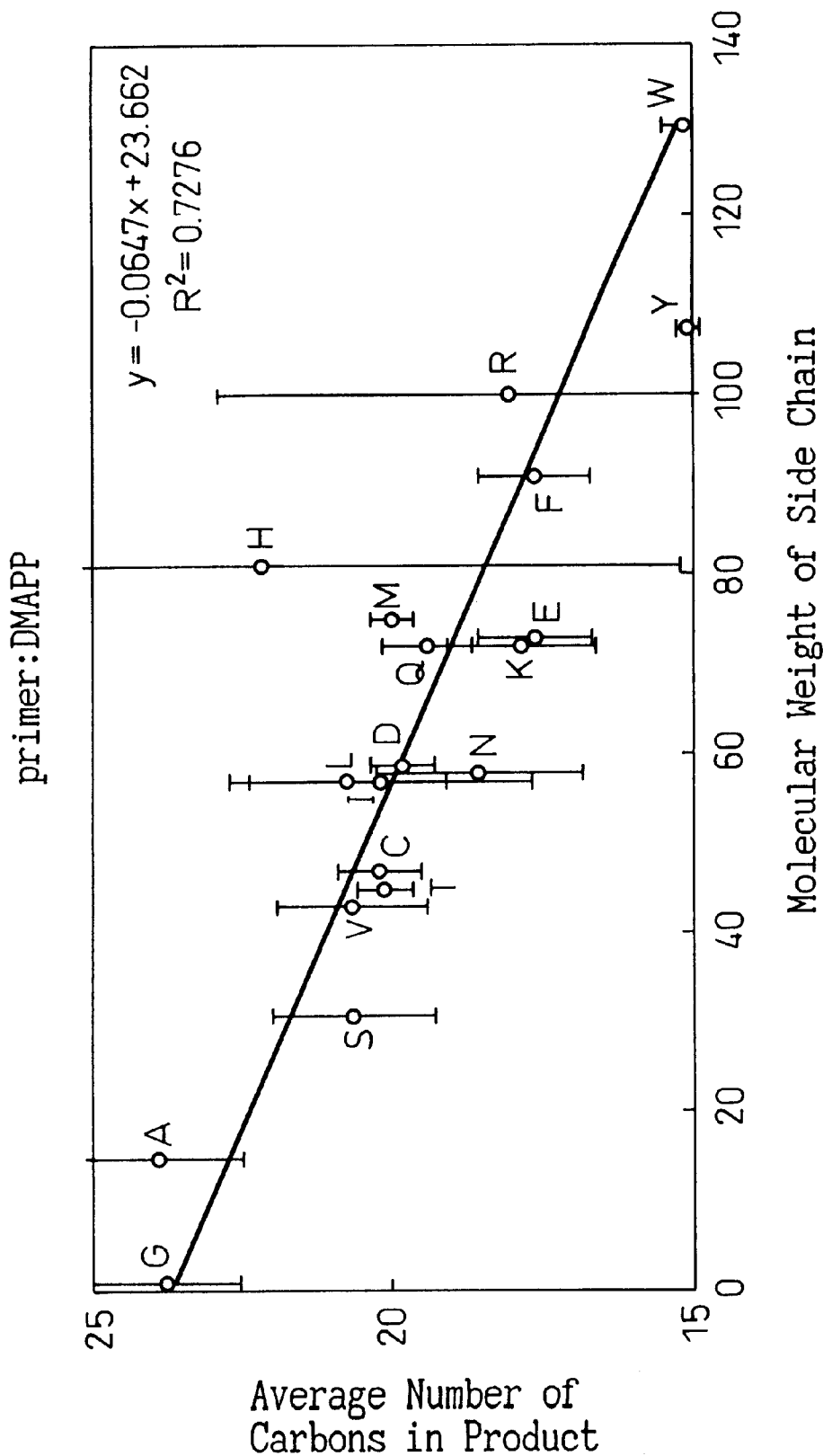
FIG. 8 is a graph showing the relationship between average chain length of the reaction products when DAMPP was used as the allylic substrate and the molecular weights of the amino acid side chains.
Figure 9:
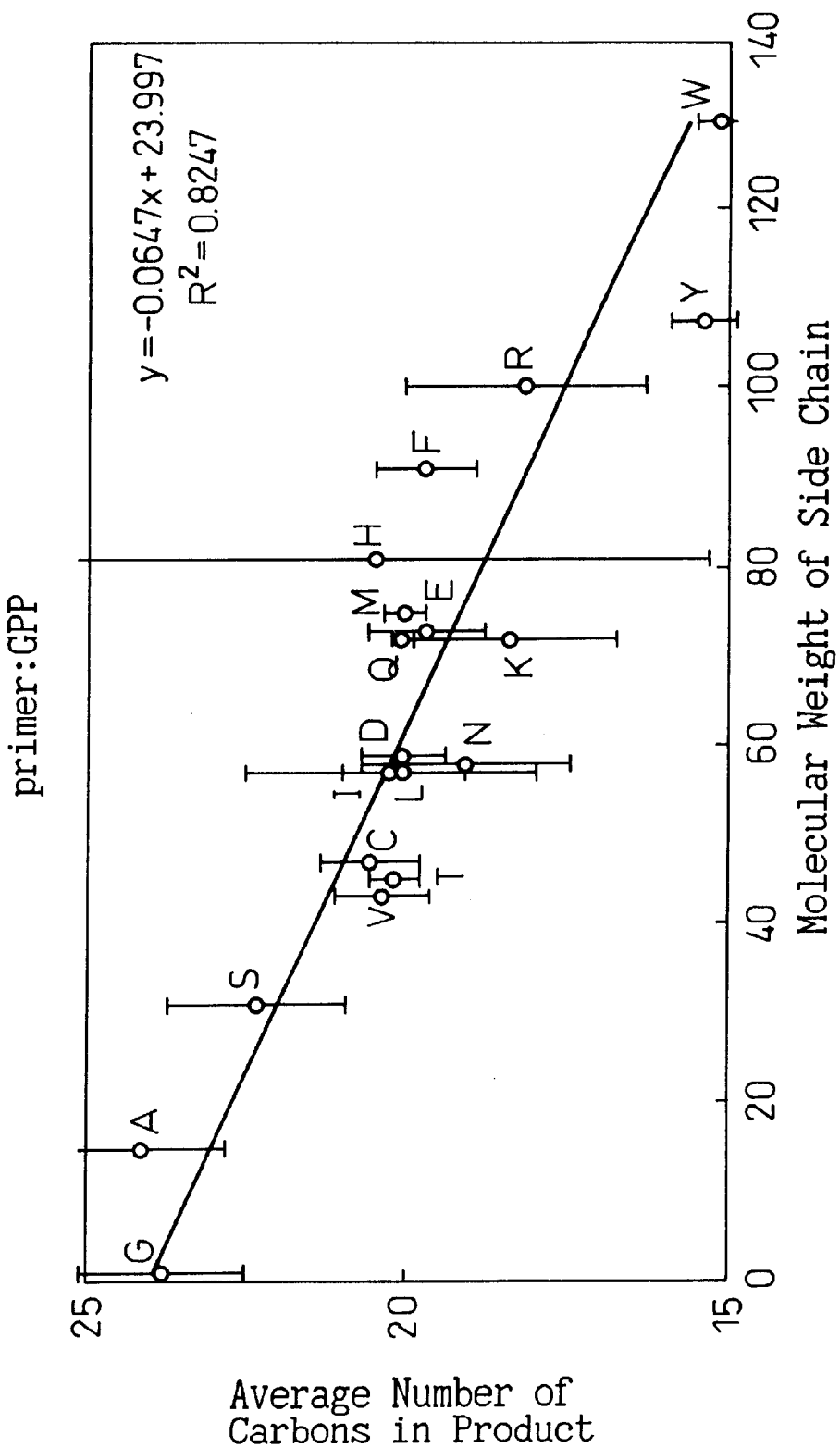
FIG. 9 is a graph showing the relationship between average chain length of the reaction products when FPP was used as the allylic substrate and the molecular weights of the amino acid side chains.

As a result, it was clearly shown that when the molecular weights of the side chains are small the activity tends to increase (FIG. 7). The tendency was also observed even when parameters other than the molecular weight of the side chain that represents the size of the amino acid residue was used, such as the accessible surface area i.e. a parameter of the exposed surface area of the amino acid residue [C. Chothia (1976) J. Mol. Biol. 195: 1–14, B. Lee and F. M. Richads (1971) J. Mol. Biol. 55: 379–400, S. Miller et al. (1987) J. Mol. Biol. 196: 641] and the like.

There have been very few reports so far indicating that the chain length of the reaction product was changed in the study on the mechanism of catalysis of FPP synthase by the introduction of site specific mutation without screening such as introduction of random mutation. The fact that the introduction of a single site-specific mutation enables such a dynamic control of the chain length of the reaction product as obtained by the present invention was completely unexpected.

Figure 5:
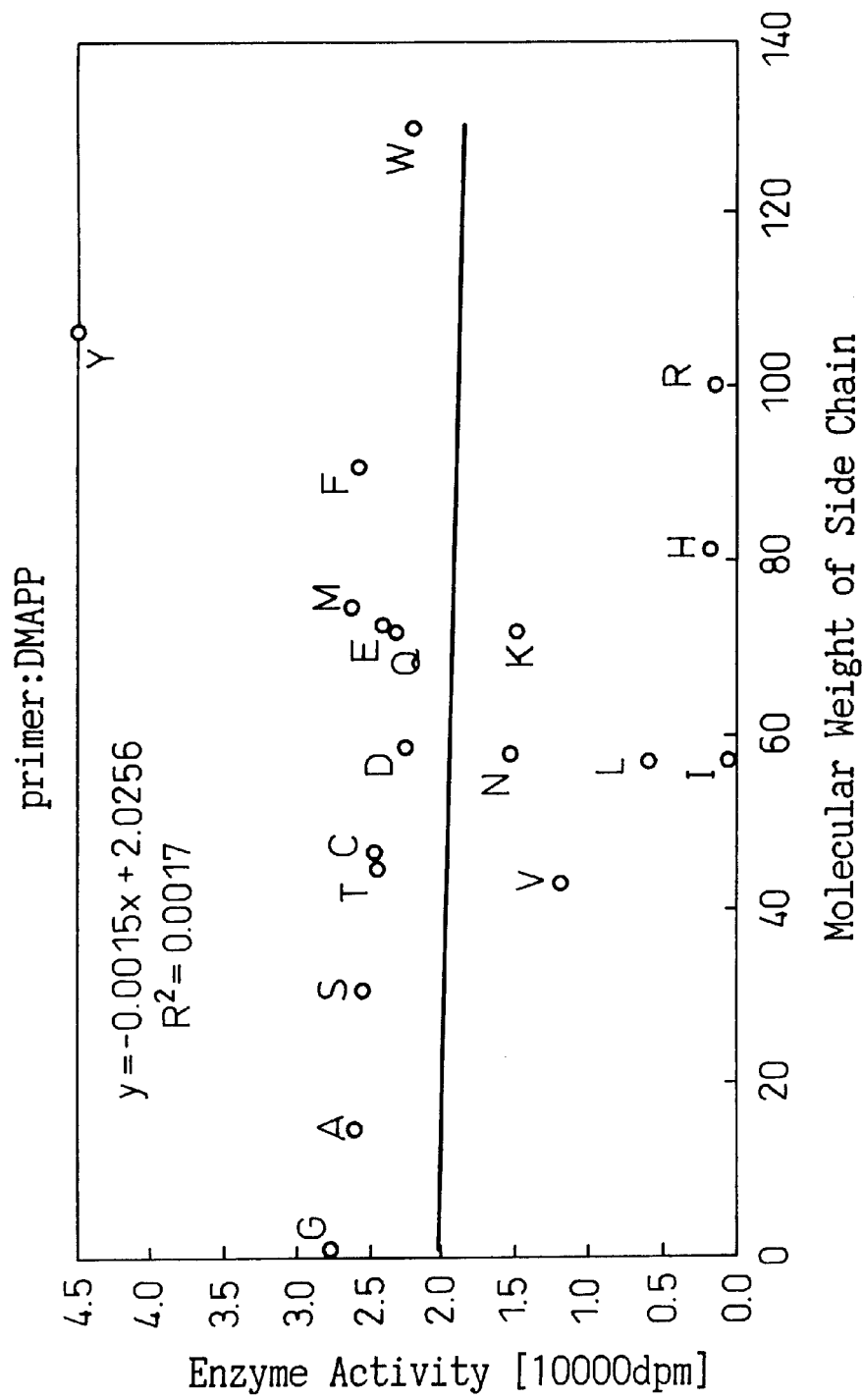
FIG. 5 is a graph showing the relationship between the enzymatic activity when DMAPP was used as the allylic substrate and the molecular weights of the amino acid side chains.
Figure 6:
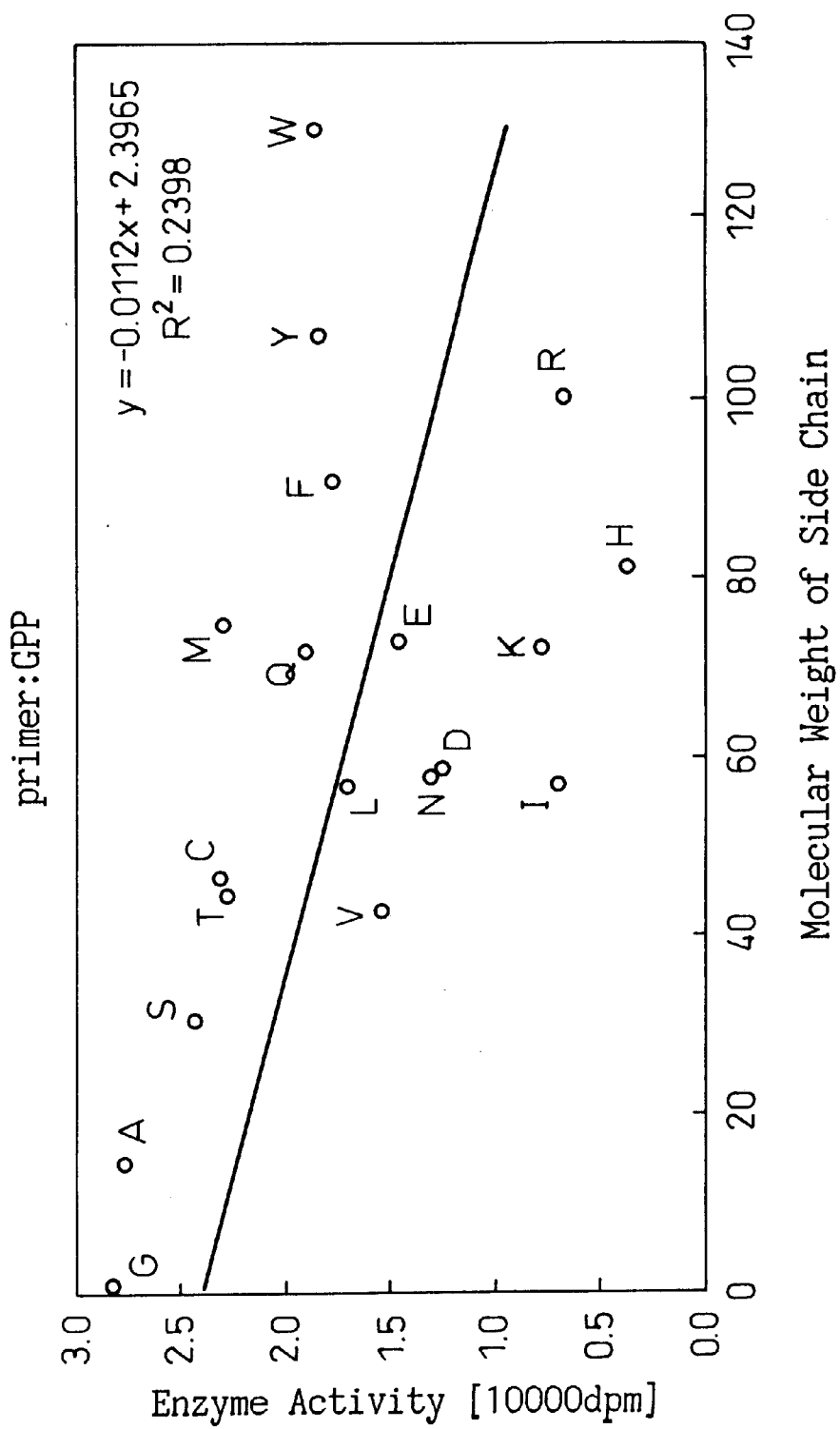
FIG. 6 is a graph showing the relationship between the enzymatic activity when GPP was used as the allylic substrate and the molecular weights of the amino acid side chains.

From FIG. 5 and 6, it can be seen that when DMAPP and GPP were used as the allylic substrate there was no significant relation between the molecular weight of the substitution-mutated amino acid residue and the enzymatic activity. This is believed to be caused by the fact that when FPP is used as the allylic substrate the reaction specificity of the wild type enzyme is directly reflected as the enzymatic activity. The specificity that uses DMAPP and GPP as the allylic substrate is inherently owned by the wild type enzyme, and therefore the analysis of tendency is difficult by the parameter of enzymatic activity alone.

Therefore, the expected value of chain length of the reaction product, that is the average chain length was obtained by the following formula:

(*the expected value of chain length of a reaction product*)=(*ratio of FPP*)×15+(*ratio of GGPP*)×20+(*ratio of GFPP*)×25+(*ratio of HexPP*)×30

The expected values obtained of the chain lengths of the reaction products were plotted against the molecular weights of the side chains of the amino acids at position 81. However, the Y81P substitution mutant enzyme in which enzymatic function was lost is excluded. It was found from these figures that the expected values of the chain length of the reaction product become higher as the molecular weight of the side chain of the amino acid residue at position 81 becomes smaller even when the allylic substrate is DMAPP or GPP.

When a similar plot analysis is made using another property of the amino acid residue at position 81, such as Hopp & Woods Scale as a parameter of hydrophobicity [J. E. Coligan et al. (1995) Current Protocols in Protein Science, Johen Wiley & Sons, Inc.] no regular tendency is observed as to the expected value of chain length of the reaction product or the enzymatic activity when FPP is used as the allylic substrate. Furthermore, even when parameters such as the ease of taking the α helix structure [J. E. Coligan et al. (1995) Current Protocols in Protein Science, Johen Wiley & Sons, Inc.] or the ease of taking the β-sheet structure [J. E. Coligan et al. (1995) Current Protocols in Protein Science, Johen Wiley & Sons, Inc.] are used, no clear relations are observed with regard to the expected value of the chain length of the reaction product or the enzymatic activity when FPP was used as the allylic substrate. It was clarified for the first time by the present invention that the factor responsible for determining the chain length of the reaction product is the size of the side chain of the amino acid residue located 5 amino acid residues upstream of the aspartic acid-rich domain I (DDXX(XX)D).

We claim:

1. An isolated DNA molecule encoding a mutant prenyl diphosphate synthase having an amino acid sequence wherein the amino acid residue Tyr at position 81 of SEQ ID NO:1 is replaced with an amino acid selected from the group consisting of Gly, Ala, Ser and Met.

2. An RNA transcribed from a DNA according to claim 1.

3. A recombinant vector comprising a DNA according to claim 1.

4. A host organism transformed by a recombinant vector according to claim 3.

5. A process for producing an enzyme encoded by the DNA molecule of claim 1 comprising culturing a host in culture medium wherein said host is transformed with an expression vector comprising an isolated DNA encoding said enzyme and then recovering expression product from the culture medium.

6. An isolated DNA molecule encoding a mutant prenvl diphosphate synthase according to claim 1 wherein said mutant prenvl diphosphate synthase is a thermostable enzyme.

* * * * *

SEQUENCE LISTING

```
<160> NUMBER OF SEQ ID NOS: 9

<210> SEQ ID NO 1
<211> LENGTH: 894
<212> TYPE: DNA
<213> ORGANISM: Bacillus stearothermophilus
<220> FEATURE:
<221> NAME/KEY: CDS
<222> LOCATION: (1)..(891)

<400> SEQUENCE: 1 gtg gcg cag ctt tca gtt gaa cag ttt ctc aac gag caa aaa cag gcg      48
Met Ala Gln Leu Ser Val Glu Gln Phe Leu Asn Glu Gln Lys Gln Ala
 1               5                  10                  15 gtg gaa aca gcg ctc tcc cgt tat ata gag cgc tta gaa ggg ccg gcg      96
Val Glu Thr Ala Leu Ser Arg Tyr Ile Glu Arg Leu Glu Gly Pro Ala
             20                  25                  30 aag ctg aaa aag gcg atg gcg tac tca ttg gag gcc ggc ggc aaa cga     144
Lys Leu Lys Lys Ala Met Ala Tyr Ser Leu Glu Ala Gly Gly Lys Arg
         35                  40                  45 atc cgt ccg ttg ctg ctt ctg tcc acc gtt cgg gcg ctc ggc aaa gac     192
Ile Arg Pro Leu Leu Leu Leu Ser Thr Val Arg Ala Leu Gly Lys Asp
     50                  55                  60 ccg gcg gtc gga ttg ccc gtc gcc tgc gcg att gaa atg atc cat acg     240
Pro Ala Val Gly Leu Pro Val Ala Cys Ala Ile Glu Met Ile His Thr
 65                  70                  75                  80 tac tct ttg atc cat gat gat ttg ccg agc atg gac aac gat gat ttg     288
Tyr Ser Leu Ile His Asp Asp Leu Pro Ser Met Asp Asn Asp Asp Leu
                 85                  90                  95 cgg cgc ggc aag ccg acg aac cat aaa gtg ttc ggc gag gcg atg gcc     336
Arg Arg Gly Lys Pro Thr Asn His Lys Val Phe Gly Glu Ala Met Ala
            100                 105                 110 atc ttg gcg ggg gac ggg ttg ttg acg tac gcg ttt caa ttg atc acc     384
Ile Leu Ala Gly Asp Gly Leu Leu Thr Tyr Ala Phe Gln Leu Ile Thr
        115                 120                 125 gaa atc gac gat gag cgc atc cct cct tcc gtc cgg ctt cgg ctc atc     432
Glu Ile Asp Asp Glu Arg Ile Pro Pro Ser Val Arg Leu Arg Leu Ile
    130                 135                 140 gaa cgg ctg gcg aaa gcg gcc ggt ccg gaa ggg atg gtc gcc ggt cag     480
Glu Arg Leu Ala Lys Ala Ala Gly Pro Glu Gly Met Val Ala Gly Gln
145                 150                 155                 160
```

```
gca gcc gat atg gaa gga gag ggg aaa acg ctg acg ctt tcg gag ctc         528
Ala Ala Asp Met Glu Gly Glu Gly Lys Thr Leu Thr Leu Ser Glu Leu
                165                 170                 175 gaa tac att cat cgg cat aaa acc ggg aaa atg ctg caa tac agc gtg         576
Glu Tyr Ile His Arg His Lys Thr Gly Lys Met Leu Gln Tyr Ser Val
            180                 185                 190 cac gcc ggc gcc ttg atc ggc ggc gct gat gcc cgg caa acg cgg gag         624
His Ala Gly Ala Leu Ile Gly Gly Ala Asp Ala Arg Gln Thr Arg Glu
        195                 200                 205 ctt gac gaa ttc gcc gcc cat cta ggc ctt gcc ttt caa att cgc gat         672
Leu Asp Glu Phe Ala Ala His Leu Gly Leu Ala Phe Gln Ile Arg Asp
    210                 215                 220 gat att ctc gat att gaa ggg gca gaa gaa aaa atc ggc aag ccg gtc         720
Asp Ile Leu Asp Ile Glu Gly Ala Glu Glu Lys Ile Gly Lys Pro Val
225                 230                 235                 240 ggc agc gac caa agc aac aac aaa gcg acg tat cca gcg ttg ctg tcg         768
Gly Ser Asp Gln Ser Asn Asn Lys Ala Thr Tyr Pro Ala Leu Leu Ser
                245                 250                 255 ctt gcc ggc gcg aag gaa aag ttg gcg ttc cat atc gag gcg gcg cag         816
Leu Ala Gly Ala Lys Glu Lys Leu Ala Phe His Ile Glu Ala Ala Gln
            260                 265                 270 cgc cat tta cgg aac gcc gac gtt gac ggc gcc gcg ctc gcc tat att         864
Arg His Leu Arg Asn Ala Asp Val Asp Gly Ala Ala Leu Ala Tyr Ile
        275                 280                 285 tgc gaa ctg gtc gcc gcc cgc gac cat taa                                 894
Cys Glu Leu Val Ala Ala Arg Asp His
    290                 295

<210> SEQ ID NO 2
<211> LENGTH: 297
<212> TYPE: PRT
<213> ORGANISM: Bacillus stearothermophilus

<400> SEQUENCE: 2

Met Ala Gln Leu Ser Val Glu Gln Phe Leu Asn Glu Gln Lys Gln Ala
  1               5                  10                  15

Val Glu Thr Ala Leu Ser Arg Tyr Ile Glu Arg Leu Glu Gly Pro Ala
             20                  25                  30

Lys Leu Lys Lys Ala Met Ala Tyr Ser Leu Glu Ala Gly Gly Lys Arg
         35                  40                  45

Ile Arg Pro Leu Leu Leu Leu Ser Thr Val Arg Ala Leu Gly Lys Asp
     50                  55                  60

Pro Ala Val Gly Leu Pro Val Ala Cys Ala Ile Glu Met Ile His Thr
 65                  70                  75                  80

Tyr Ser Leu Ile His Asp Asp Leu Pro Ser Met Asp Asn Asp Asp Leu
                 85                  90                  95

Arg Arg Gly Lys Pro Thr Asn His Lys Val Phe Gly Glu Ala Met Ala
            100                 105                 110

Ile Leu Ala Gly Asp Gly Leu Leu Thr Tyr Ala Phe Gln Leu Ile Thr
        115                 120                 125

Glu Ile Asp Asp Glu Arg Ile Pro Pro Ser Val Arg Leu Arg Leu Ile
    130                 135                 140

Glu Arg Leu Ala Lys Ala Ala Gly Pro Glu Gly Met Val Ala Gly Gln
145                 150                 155                 160

Ala Ala Asp Met Glu Gly Glu Gly Lys Thr Leu Thr Leu Ser Glu Leu
                165                 170                 175

Glu Tyr Ile His Arg His Lys Thr Gly Lys Met Leu Gln Tyr Ser Val
            180                 185                 190
```

```
His Ala Gly Ala Leu Ile Gly Gly Ala Asp Ala Arg Gln Thr Arg Glu
            195                 200                 205

Leu Asp Glu Phe Ala Ala His Leu Gly Leu Ala Phe Gln Ile Arg Asp
    210                 215                 220

Asp Ile Leu Asp Ile Glu Gly Ala Glu Lys Ile Gly Lys Pro Val
225                 230                 235                 240

Gly Ser Asp Gln Ser Asn Asn Lys Ala Thr Tyr Pro Ala Leu Leu Ser
                245                 250                 255

Leu Ala Gly Ala Lys Glu Lys Leu Ala Phe His Ile Glu Ala Ala Gln
            260                 265                 270

Arg His Leu Arg Asn Ala Asp Val Asp Gly Ala Ala Leu Ala Tyr Ile
            275                 280                 285

Cys Glu Leu Val Ala Ala Arg Asp His
            290                 295
```

<210> SEQ ID NO 3
<211> LENGTH: 34
<212> TYPE: DNA
<213> ORGANISM: Artificial Sequence
<220> FEATURE:
<223> OTHER INFORMATION: Description of Artificial Sequence: synthetic
      DNA
<220> FEATURE:
<223> OTHER INFORMATION: "n" at positions 11...13 may be A, T, C, G,
      other or unknown

<400> SEQUENCE: 3
gatccatacg nnntctttga ttcatgatga tttg                            34

<210> SEQ ID NO 4
<211> LENGTH: 34
<212> TYPE: DNA
<213> ORGANISM: Artificial Sequence
<220> FEATURE:
<223> OTHER INFORMATION: Description of Artificial Sequence: synthetic
      DNA

<400> SEQUENCE: 4
gatccatacg aactctttga ttcatgatga tttg                            34

<210> SEQ ID NO 5
<211> LENGTH: 34
<212> TYPE: DNA
<213> ORGANISM: Artificial Sequence
<220> FEATURE:
<223> OTHER INFORMATION: Description of Artificial Sequence: synthetic
      DNA

<400> SEQUENCE: 5
gatccatacg atttctttga ttcatgatga tttg                            34

<210> SEQ ID NO 6
<211> LENGTH: 34
<212> TYPE: DNA
<213> ORGANISM: Artificial Sequence
<220> FEATURE:
<223> OTHER INFORMATION: Description of Artificial Sequence: synthetic
      DNA

<400> SEQUENCE: 6
gatccatacg atgtctttga ttcatgatga tttg                            34

<210> SEQ ID NO 7

-continued

```
<211> LENGTH: 34
<212> TYPE: DNA
<213> ORGANISM: Artificial Sequence
<220> FEATURE:
<223> OTHER INFORMATION: Description of Artificial Sequence: synthetic
                        DNA

<400> SEQUENCE: 7
gatccatacg ttctctttga ttcatgatga tttg                              34

<210> SEQ ID NO 8
<211> LENGTH: 34
<212> TYPE: DNA
<213> ORGANISM: Artificial Sequence
<220> FEATURE:
<223> OTHER INFORMATION: Description of Artificial Sequence: synthetic
                        DNA

<400> SEQUENCE: 8
gatccatacg ccgtctttga ttcatgatga tttg                              34

<210> SEQ ID NO 9
<211> LENGTH: 34
<212> TYPE: DNA
<213> ORGANISM: Artificial Sequence
<220> FEATURE:
<223> OTHER INFORMATION: Description of Artificial Sequence: synthetic
                        DNA

<400> SEQUENCE: 9
gatccatacg gtgtctttga ttcatgatga tttg                              34
```